United States Patent

Fox et al.

[11] Patent Number: 5,219,121
[45] Date of Patent: Jun. 15, 1993

[54] DEVICE FOR THE EVAPORATION OF VOLATILE LIQUIDS

[75] Inventors: Rodney T. Fox; Geoffrey R. Hammond, both of Hull, Great Britain

[73] Assignee: Reckitt & Colman Products Limited, London, Great Britain

[21] Appl. No.: 828,816
[22] PCT Filed: Aug. 13, 1990
[86] PCT No.: PCT/GB90/01264
§ 371 Date: Jan. 27, 1992
§ 102(e) Date: Jan. 27, 1992
[87] PCT Pub. No.: WO91/02549
PCT Pub. Date: Mar. 7, 1991

[30] Foreign Application Priority Data

Aug. 26, 1989 [GB] United Kingdom ............... 8919463

[51] Int. Cl.[5] .................................................. A61L 9/12
[52] U.S. Cl. ............................................. 239/43; 239/34; 239/57
[58] Field of Search .......................... 239/34, 35, 37, 43, 239/44, 57

[56] References Cited

U.S. PATENT DOCUMENTS

| | | | |
|---|---|---|---|
| 1,043,159 | 11/1912 | Sleeper | 239/44 |
| 2,766,066 | 10/1956 | Hopson et al. | 239/44 X |
| 4,094,119 | 6/1978 | Sullivan | 53/4 |
| 4,583,686 | 4/1986 | Martens et al. | 239/35 |
| 4,634,614 | 1/1987 | Holzner | 239/57 X |
| 4,753,389 | 6/1988 | Davis | 239/6 |
| 4,898,328 | 2/1990 | Fox et al. | 239/6 |
| 4,917,301 | 4/1990 | Munteneau | 239/43 |
| 4,948,047 | 8/1990 | Zembrodt | 239/34 |
| 4,995,555 | 2/1991 | Woodruff | 239/43 |

FOREIGN PATENT DOCUMENTS 0093262  11/1983  European Pat. Off.
0200493  11/1986  European Pat. Off.
0218892  4/1987   European Pat. Off.

Primary Examiner—Andres Kashnikow
Assistant Examiner—William Grant
Attorney, Agent, or Firm—Rosen, Dainow & Jacobs

[57] ABSTRACT

A device for dispensing any one of a wide range of volatile liquids as vapours, comprises a reservoir with an open end closed by a vapor-permeable, liquid-impermeable element. A flange surrounds the opening to the reservoir and the element is bondable to the flange in a multiplicity of different locations, each of which defines a respective area of the element bounded by the bond and wettable by the volatile liquid. Thus, a single device can be used to dispense any one of a wide range of volatile materials simply by determining the surface area within the bond to be wetted by the volatile liquid to give the desired rate of vapor release for the selected volatile material and bonding the element to the flange in a location to define the determined wettable area of the element.

23 Claims, 3 Drawing Sheets

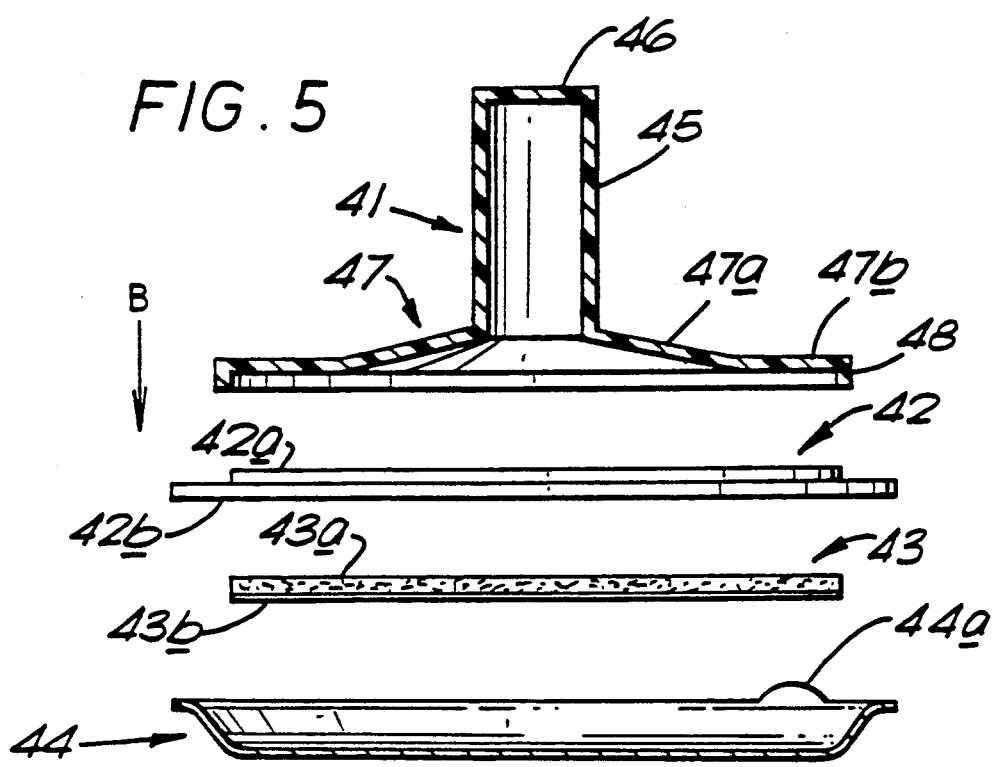
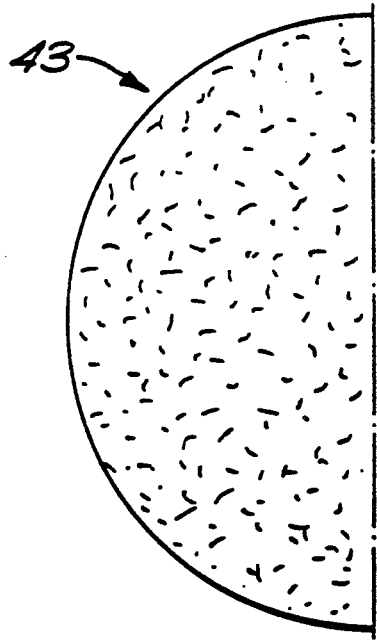 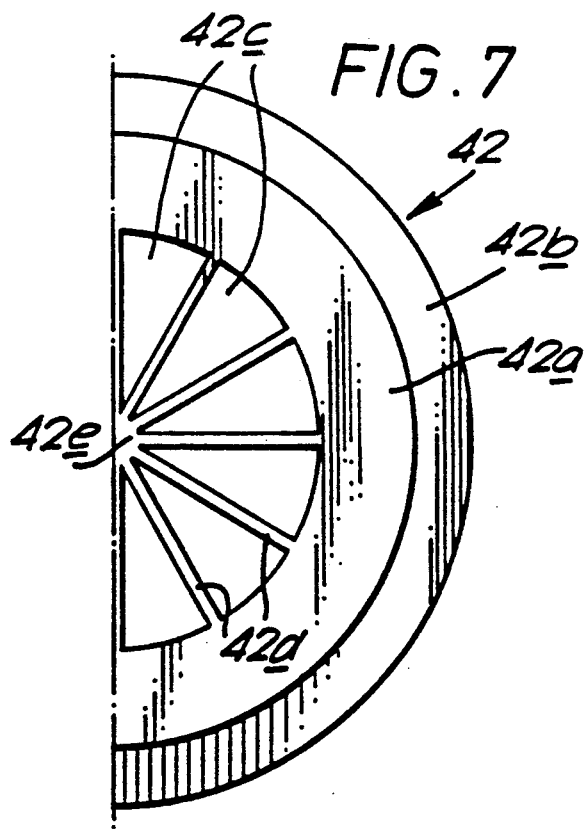

DEVICE FOR THE EVAPORATION OF VOLATILE LIQUIDS

FIELD OF THE INVENTION

This invention is concerned with improvements in the dispensing of volatile liquid substances as vapours and has particular application to the controlled release of such volatile liquids as perfumes and the like; air fresheners; liquid insecticides; liquid insect repellents; liquid deodorants; liquid corrosion inhibitors; germicidal agents; and medicants such as respiration-aiding liquids.

BACKGROUND OF THE INVENTION

Devices for dispensing volatile liquids as vapours are well known in the art and conventionally comprise a reservoir housing for containing the volatile liquid and an element for releasing volatile liquid vapours into the atmosphere.

All such prior art devices fall into one or another of three basic groups:

(1) Devices wherein the reservoir housing comprises the element for releasing the volatile liquid vapours to the surrounding atmosphere, (2) devices wherein the reservoir housing is relatively rigid and the element for releasing volatile liquid vapours is displaceable relative to said reservoir housing, and (3) devices wherein the reservoir housing is relatively rigid and the element for releasing volatile liquid vapours is fixed relative to said reservoir housing.

The present invention is concerned only with group (3) devices and all groups (1) and (2) dispensing devices are disclaimed herefrom.

Devices falling into group (3) are marketed in many different forms and conventionally such devices comprise a substantially rigid reservoir housing, for containing the volatile liquid, closed at one end by a vapour-permeable element. Such a device is, hereinafter, referred to as "a device of the type defined".

Devices of the type defined are marketed in many different shapes and sizes and can be used in different ways.

The U.S. Pat. No. 4,753,389 discloses a vaporizing device of the type defined (see FIG. 5) in which the reservoir housing comprises a tubular element, closed at one end by a rigid wall and at its other end by a vapour-permeable element. The reservoir is charged with a volatile liquid and, in use, the device is located with the vapour-permeable element uppermost, whereby a plenum chamber or space is formed between the volatile liquid and the vapour-permeable element. The volatile liquid evaporates into said plenum and is released through the vapour-permeable element to the surrounding atmosphere.

The European Patent Publication No. 0218892 discloses a vaporizing device of the type defined comprising a reservoir housing in the form of a tubular element, closed at one end by a rigid wall and closed at its other end by a vapour-permeable, liquid-impermeable element. The reservoir is charged with a volume of the volatile liquid to be dispensed and, in use, the device is positioned with the said element lowermost, whereupon the volatile liquid wets the inner surface of the vapour-permeable, liquid-impermeable element and evaporates through the said element to escape from the external surface of said element to the surrounding atmosphere.

A third dispensing arrangement of the type defined is disclosed in British Patent Publication No. 2194889B and wherein a housing, in the form of a tubular element, is closed at one end by a rigid wall and at the other end by a vapour-permeable, liquid-impermeable element.

In this third mode of use (see FIG. 1 of the publication) the housing rests on its cylindrical wall so that the said element is substantially vertical. A head space above the free surface of the volatile liquid in the housing is charged with evaporated volatile liquid and the vapours escape through the said element above the free surface of the volatile liquid, whilst liquid entering the element below the free surface of the liquid is vaporized and passes through the said element below the free surface of the liquid.

It should be noted that in all three of the above recited examples, and in most commercially available devices of the type defined, the cross-sectional area of the reservoir is substantially constant at right angles to the plane of the vapour-permeable element and this cross-sectional area is substantially equal to the cross-sectional area of the vapour-permeable element exposed to the volatile material, be this in liquid or vapour form.

As each volatile liquid capable of being dispensed as a vapour will have a rate of vaporization, and a desired rate of release of vapours, individual to that liquid the only variables available in the prior art devices for varying the rate of vaporization and the rate of vapour release is to vary the size of the reservoir housing, which leads to a wide variety of differently sized housings, and/or varying the formulation of the volatile liquid to be contained in the reservoir housing, and which leads to larger volumes of liquid to be contained in the reservoir housing and often the introduction of unnecessary and undesirable impurities in the contained volatile liquids.

A further problem with many prior art devices of the type defined, and in particular the form of device disclosed in the U.S. Pat. No. 4,753,389 and the British Patent Publication No. 2194889B, arises in that many of the volatile liquids dispensable as vapours comprise complex blends of volatile ingredients. With a gas volume above the free surface of the liquid the more volatile of said ingredients can vaporize into the said gas volume more readily than the less volatile materials and can pass through the porous element above so that the composition of the vapours can vary throughout the life of the device.

The present invention seeks to provide a device of the type defined and for which the rate of vaporization of the volatile liquid can be adjusted without varying the dimensions of the reservoir housing.

SUMMARY OF THE INVENTION

According to the present invention there is provided a device, for dispensing any one of a wide range of different volatile liquids as a vapour, comprising a reservoir housing defining a reservoir open at one end and a vapour-permeable element bonded to said housing to close the open end of said reservoir, characterized in that said reservoir housing defines an outwardly extending flange surrounding the open end of said reservoir and the vapour-permeable element is bonded to the said flange to expose an area of the vapour-permeable element bounded by the bond, wettable by the volatile liquid in the reservoir and capable of affording the desired rate of evaporation for the selected volatile liquid to be dispensed.

Preferably said flange is an annular flange, the vapour-permeable element has a circular periphery, said element is bonded to the flange along an annulus of said element and the inner diameter of said annular bond is variable to vary the area of the vapour-permeable element within the said inner diameter wettable by the volatile liquid.

Preferably the area of the flange engageable by the said vapour-permeable element is greater than twice, and more preferably greater than four times, the greatest cross-sectional area of the reservoir in planes parallel with the said flange.

Preferably said vapour-permeable element comprises a liquid-impermeable element.

In one embodiment in accordance with the invention said vapour-permeable element is of laminate construction comprising a liquid-permeable layer and a vapour-permeable, liquid-impermeable layer.

In one embodiment the said bonding of said vapour-permeable element to said flange is effected by an adhesive material.

In a preferred embodiment according to the invention the opening of said reservoir housing, closed by the vapour-permeable element, has a greater area than the mean cross-sectional area of the reservoir in planes parallel to the plane of the vapour-permeable element.

Preferably the said reservoir housing defines two reservoir parts in open communication, a first reservoir part being adjacent the vapour-permeable element and the second reservoir part being remote from the said vapour-permeable element, said first reservoir part having a mean cross-sectional area greater than the mean cross-sectional area of the second reservoir part in planes parallel to said vapour-permeable element.

Preferably the central axes of said first and second reservoir parts lie on a common axis.

Preferably said first reservoir part reduces in cross-sectional area, in planes parallel to said vapour-permeable element, from the plane of said element towards the second reservoir part.

In a preferred embodiment said second reservoir part is of substantially uniform cross-section in planes parallel to the plane of said vapour-permeable element.

Preferably the mean cross-sectional area of the second reservoir part is less than 80%, and more preferably less than 60%, of the mean cross-sectional area of the first reservoir part in planes parallel to said vapour-permeable element.

In a preferred embodiment the said flange includes two annular regions, an outer annular region lying in a plane at right angles to the axis of said reservoir and to which the vapour-permeable element is bonded, and an inner annular region defining the first reservoir part.

Preferably the inner annular regions of said flange spaces the plane of the outer annular region of said flange from the second reservoir.

In a preferred embodiment the device is characterised by support means arranged to support that area of the vapour-permeable element exposed to the reservoir.

In one embodiment the said support means comprise ribs presented by said flange.

In another embodiment said support means comprise a support member between said reservoir housing and said vapour-permeable element.

Preferably said support member is bonded to said vapour-permeable element and to said reservoir housing.

Preferably the support member is moulded integral with said vapour-permeable element.

In a preferred embodiment said support member defines a plurality of apertures through its thickness and areas of the said element exposed through said apertures are exposed to wetting by the volatile liquid in said reservoir.

The invention also envisages a device for dispensing a volatile liquid as a vapour in accordance with the invention in combination with a holder for the device, characterised in that the holder is arranged to totally enclose the device and support the device with its vapour-permeable element lowermost and exposed to a volume within said holder and said holder including apertures which vent said volume to the surrounding atmosphere.

Preferably the said holder comprises a base part, within which device the device is supported, and a removable lid which, when removed, allows a device to be placed into, or removed from, the holder.

DETAILED DISCLOSURE

The invention will now be described further by way of example with reference to the accompanying drawings in which, FIG. 1 shows an axial exploded cross-sectional view of a device of the type defined in accordance with the invention, FIG. 2 shows a view of the device illustrated in FIG. 1 in the direction of the Arrow A, FIG. 3 shows a detail cross-sectional view through a bonding of the flange and vapour-permeable element.

FIG. 5 shows an axial, exploded view of a second device of the type defined in accordance with the invention, FIG. 6 shows a view, to one side of the centre-line, of the vaporizing element in FIG. 5 in the direction of the Arrow B.

FIG. 7 shows a view, to one side of the centre-line, of the support member in FIG. 5 in the direction of the Arrow B.

Figure 1:
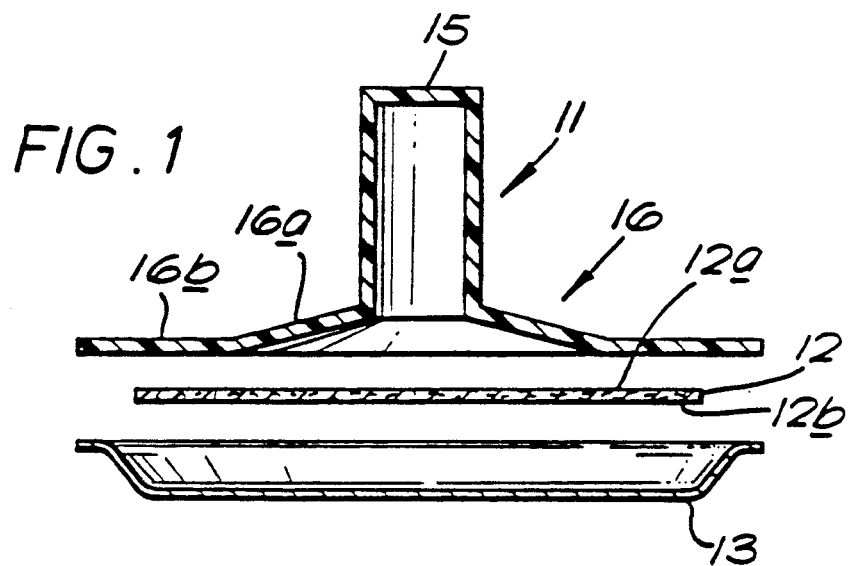
Figure 2:
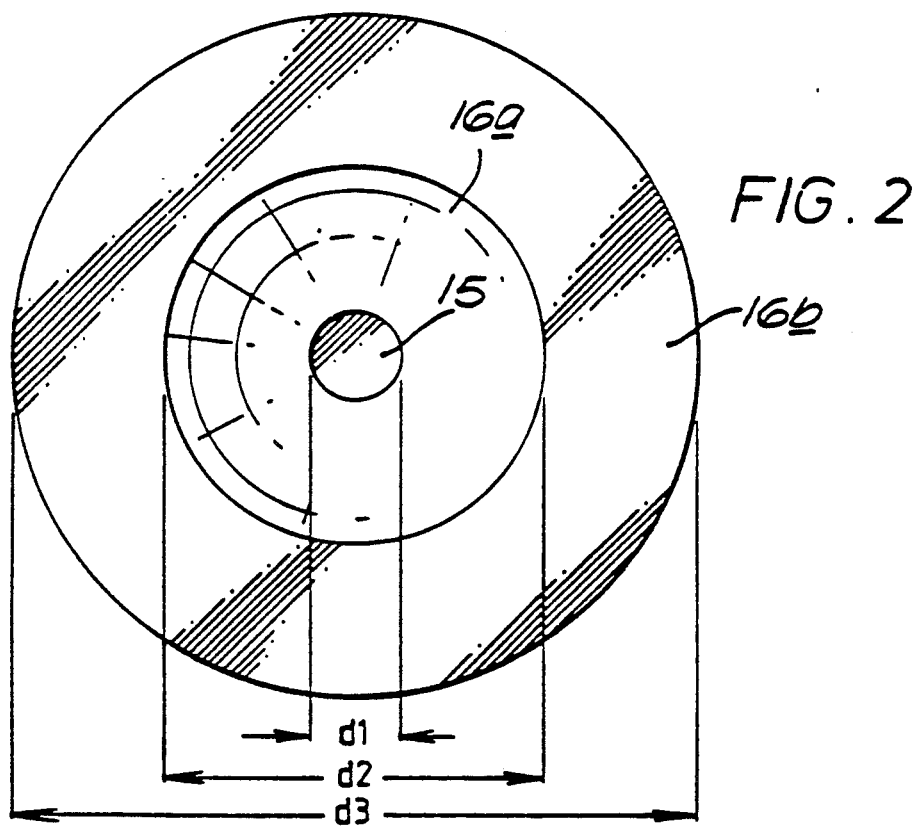
Figure 3:
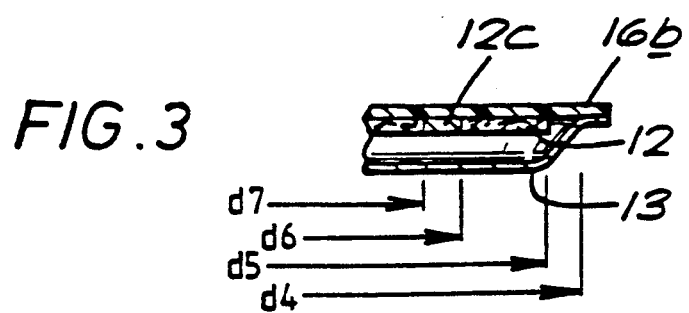

The device shown in FIGS. 1, 2 and 3 of the drawings generally comprises a reservoir housing 11, a vapour-permeable, liquid-impermeable element 12 and a liquid-impermeable vapour-impermeable barrier element 13.

The casing 11 comprises a body of revolution defined by a cylindrical wall 14, closed at one end by a rigid end wall 15, with a flange 16 extending generally radially from that end of the cylindrical wall 14 remote from the end wall 15.

As will be most readily seen from FIGS. 1 and 2 the flange 16 comprises an inner annular region 16a, between diameters d1 and d2, which slopes downwardly and outwardly from the lower regions of the cylindrical wall 14 (as viewed in FIG. 1), so as to be inclined to the horizontal when the axis of the cylindrical wall 14 is vertical. The flange 16 further includes an outer annular region 16b, between diameters d2 and d3, lying in a plane at right angles to the axis of the cylindrical wall 14. Preferably the cross-sectional area of the flange 16b on that side of flange 16 to be contacted by the element 12 is greater than twice the cross-sectional area of the reservoir opening at the said flange side.

The reservoir housing 11 may conventionally be made from any material, inert with respect to the volatile liquid to be dispensed, but preferably said casing 11 comprises a plastics material, most preferably a see-through plastics material and through which the level of volatile liquid within the reservoir housing 11 can be readily seen.

The vapour-permeable, liquid-impermeable element 12 is of annular, planar form and presents parallel major faces 12a and 12b. Said element 12 is made from any natural or synthetic material, inert with respect to the volatile liquid and capable of preventing flow of the volatile liquid through its thickness whilst permitting the flow of volatile liquid vapour therethrough.

Thus, for example, the element 12 may comprise a sintered body having fine pores, which allow the volatile liquid to enter the element 12 through the inner surface 12a therein but so delays the passage of the liquid that said liquid vaporizes in said pores before the said liquid can reach the surface 12b remote from the wetted surface 12a.

In another form the said element 12 may be of composite construction comprising a body of a material, which allows the flow of liquid through its thickness with a laminate or coating of a material, capable of blocking the flow of liquid therethrough whilst permitting the flow of vapour therethrough, forming the external major surface 12b of the laminate.

Such a composite material may conveniently comprise a porous sheet of paper treated on its surface 12b, with a material, for example a substantially elastomeric crosslinked organopolysiloxane (silicone) material, to render said surface 12b impermeable to the liquid and yet permit the passage of vapours therethrough.

The paper must be robust and mechanically strong and must also have a high wet strength, as the evaporation of volatile liquid at a higher rate than its replacement by air can cause cavitation in the element 12.

The paper in effect is acting as wick, allowing the volatile liquid to pass to the coating defining the exterior surface 12b of the element 12.

Many types of porous paper were found not to be readily coatable with the organopolysiloxane material, as the siloxane is applied wet and is easily absorbed. Coated papers that were tested and found to be successful as vapour-permeable, volatile-liquid-impermeable elements 12 include COTEK 85A, an 85 g m$^{-2}$ bleached release paper coated on one side with silicone, supplied by Cotek Papers Ltd., Draycott, Gloucestershire, UK; and STERA-LEASE 13, a 130 gm$^{-2}$ release paper coated on one side with silicone, supplied by Sterling Coated Materials Ltd., Hollingworth, Cheshire, UK.

It was discovered that using a thick paper did not substantially affect the operation of the device, as there was no effect on wicking or evaporation rates; but problems associated with cavitation that had been encountered with thinner papers were avoided. Increasing the thickness of the coating of organopolysiloxane material did not eliminate cavitation when this was encountered.

The barrier element 13 is dish-shaped and has its peripheral edges sealed, in a peelable manner, to the peripheral regions of the flange part 16b of the reservoir housing 11. The peelable barrier element 13 is conveniently made from a metallic foil membrane, for example a polyester-aluminum laminate, coated with a low temperature heat seal lacquer.

The vapour-permeable, liquid-impermeable element 12 has an outer diameter d5 less than the diameter d4 of the innermost regions of the connection to be affected between the flange 16b and the peelable barrier 13. The element 12 is bonded to the flange 16b over an annular region 12c of said element 12 between diameters d6 and d7, which is calculated to define an area of the surface 12a of the element 12 within the diameter d7 of the annular bonding and which has been predetermined to obtain the desired rate of release of the vapours for the volatile liquid contained in the housing 11.

Thus, the diameters of the annular bonding 12c can be varied between an internal diameter d7 equal to the diameter d2, and an external diameter d6 equal to the diameter d5 and the area of the surface 12a within the diameter d7 of the annular bonding, and which area will be wetted by the volatile liquid within the reservoir, can thereby be varied to obtain a desired rate of vapour issue from the element 12 for any one of a wide range of different volatile liquids.

Bonding of the element 12 to the flange 16b may be achieved using a suitable adhesive and in such case the adhesive will enter at least partially through the thickness of the element 12 in the vicinity of the bond and will substantially reduce the flows of volatile liquid within the bonded region radially outwardly of the diameter d7.

Some liquid and vapours will flow radially outwardly through the annular bonding 12c for release through the surface 12b as vapour but the area of the laminate 12 exposed to wetting directly by the volatile liquid in the reservoir is restricted to the area of the laminate 12 with the radius d7.

The reservoir housing 11 may be charged with volatile material by inverting the reservoir housing 11 from the position shown in FIG. 1, charging the reservoir housing 11 with the volatile liquid to be dispensed, and sealing the vapour-permeable, liquid-impermeable element 12 to the flange 16b. The peelable vapour-impermeable barrier 13 can then be attached to the flange 16b, conveniently by a low temperature heat sealing process.

In an alternative method for charging the reservoir the vapour-permeable, volatile liquid impermeable element 12 is bonded to the flange 16b, the peelable barrier 13 is then affixed to the flange 16b and the reservoir is charged through an aperture (not shown) in the end wall 15 and which aperture will then be sealed with a non-peelable foil, for example an aluminium foil laminated with polyester, to prevent the loss of volatile liquid and volatile liquid vapours through said aperture.

The device illustrated in FIGS. 1, 2 and 3 is especially useful when a small volume of volatile liquid is to be evaporated, as the relatively large area of the surface 12a of the laminate 12 wettable by the liquid compared with the volume of the reservoir gives a high evaporation rate. Neat fragrance without solvents may be used for the volatile liquid and this has the advantage that fractionation of components of the fragrance formulation does not occur during evaporation and the composition of the vapours remains constant over a period of time. End of use may be detected by inspection of the housing 11 if this is made of transparent or translucent material.

With the volatile liquid sealed within the reservoir the device is easy and safe to handle and can have a relatively long shelf life.

To use the device the peelable barrier element 13 is peeled off and the device is supported in the position shown in FIG. 1, whereupon the reservoir of volatile liquid is above the vapour-permeable, liquid-impermeable element 12 and the whole of that area of the element 12 within the diameter d7 is exposed to wetting by the volatile material in the reservoir; that area of the element 12 within the diameter d2, being directly exposed to the volatile liquid in the reservoir and that annular region of the element 12 between the diameter d2 and d7, being wetted by volatile liquid creeping between the flange 16b and the element 12 and by internal flows of volatile liquid within the element 12.

The device is suspended or supported such that the element 12 is exposed to the atmosphere. When the volatile liquid from the reservoir wets the upper surface 12a of the element 12 said liquid flows downwardly and transversely, through the element 12 to the surface 12b and at said surface the volatile liquid vaporizes and is released through the surface 12b into the surrounding atmosphere.

It should now be noted that the reservoir housing 11 defines two reservoir parts in open communication, that reservoir part within the cylindrical wall 14 and that reservoir part within the annular region 16a of the flange 16.

The reservoir part defined within the annular region 16a of the flange 16, hereinafter referred to as the first reservoir part, is closed by the vapour-permeable vapour element 12 sealed to the annular flange part 16b and the diameter d2 defines the largest area of the reservoir in planes parallel to the element 12. As will be seen from FIGS. 1 and 2 the cross-sectional area of the said first reservoir part progressively reduces to the diameter d1 in planes parallel to the element 12.

The cross-sectional area of the reservoir part within the cylindrical wall 14, hereinafter referred to as the second reservoir part, is substantially constant in planes parallel to the element 12.

Thus, the mean cross-sectional area of the first reservoir part is greater than the mean cross-sectional area of the second reservoir part in planes parallel to the element 12 and the mean cross-sectional area of the second reservoir part is preferably less than 80%, and more preferably less than 60%, of the mean cross-sectional area of the first reservoir part in planes parallel to the element 12.

This means that, when the device is in its position of use with the element 12 lowermost, any gaseous volume within the reservoir will lie above the free surface of the volatile liquid within the second reservoir part and the area of the free surface of the volatile liquid exposed to the head space will be the smallest area possible for all the positions of the device.

As volatile liquid from the reservoir is vaporized and released through the element 12 to atmosphere the level of the liquid in the reservoir falls, so that the gaseous volume above the free surface of the volatile liquid increases and the pressure in said head space can fall.

As the pressure in the head space falls volatile liquid evaporates from the free surface of the volatile liquid within the reservoir but, when all the volatile ingredients in the volatile liquid are distributed throughout the body of the volatile liquid, the selective vaporization of the most readily evaporated constituents into the head space is kept to a minimum so that variations in the vapours emitted through the element 12 remain relatively constant throughout the life of the device.

The evaporation of the volatile liquid into the head space assists in preventing the pressure within the head space from falling below that level at which the volatile liquid will wet the whole of the volume of the element 12 within the diameter d7 but, in the event, should the pressure in said head space fall below that pressure at which the liquid flows readily through the thickness of the element 12 air will enter the system through the vapour-permeable, liquid-impermeable surface 12b and flow upwardly through the volatile liquid to the head space.

Figure 8:
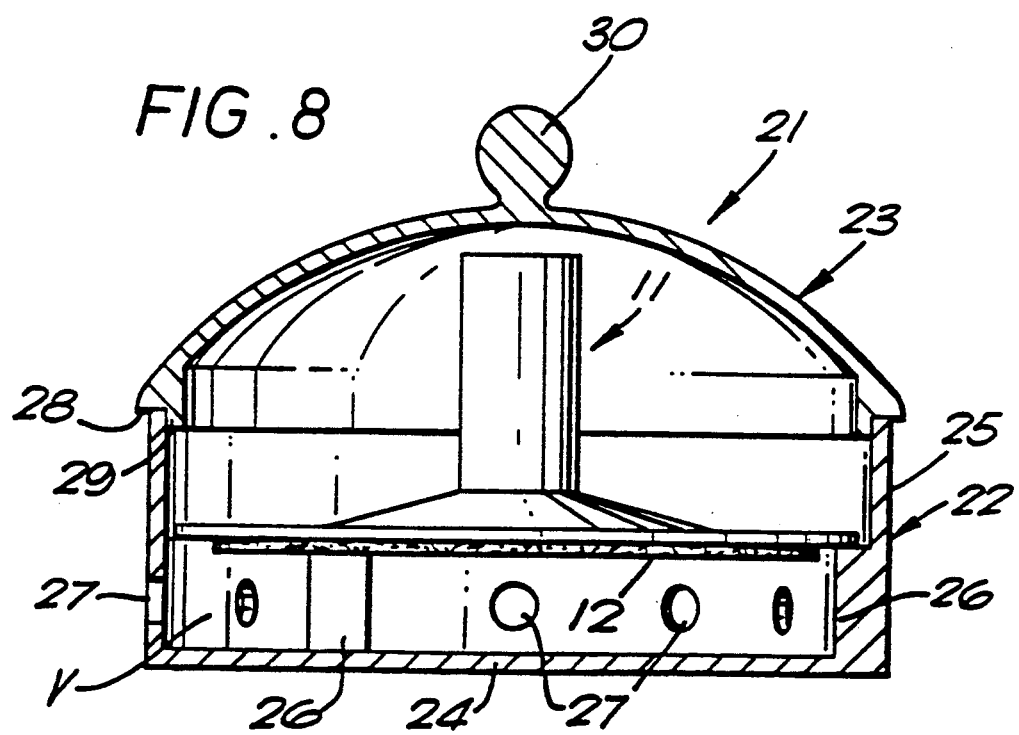
FIG. 8 shows a centre-line cross-section through a holder for a device in accordance with the invention.

FIG. 8 shows one form for a holder 21 which may be used to support the device illustrated in FIG. 1 for the evaporation of volatile liquids.

The holder 21 comprises a base part 22 and a decorative lid part 23. The base part 22 comprises a bottom wall 24 with an upstanding cylindrical wall 25 and with three ribs 26 extending upwardly from the bottom wall 24, integral with the cylindrical wall 25, and which ribs 26 terminate in a common plane parallel with the bottom wall 24.

The internal diameter of the cylindrical wall 25 above said ribs 26 is slightly larger than the external diameter of the flange 16 of a device, whereupon a device 11 to 16 inclusive as shown in FIG. 1, may be entered into the base part 22, as shown in FIG. 8.

The ribs 26 protrude radially within the cylindrical walls 25 sufficient to form abutment surfaces for the peripheral regions of the flange 16 of the device 11 to 16 inclusive, but not sufficient as to make contact with the element 12, whereupon the whole of the undersurface 12b of the element 12 is open to the atmosphere in the volume V between the element 12 and the bottom wall 24. Thus, volatile liquid vapours passing through the surface 12b of the element 12 are released into the atmosphere in the volume V and therefrom to the surrounding atmosphere via apertures 27 through the cylindrical wall 25.

The lid 23 presents a radially extending abutment surface 28, which rests on the free radial surface of the cylindrical wall 25, and an axially extending wall 29 has a diameter slightly smaller than the internal diameter of the cylindrical wall 25 above the ribs 26, so that the axially extending wall 29 can enter into the cylindrical wall 25.

The top 23 is provided with a knob 30 by which the lid 23 can be removed from the bottom 22 to allow an exhausted device 11 to 16 inclusive to be removed and replaced by a new device 11 to 16.

When the device has been in use for a period of time and volatile liquid has vaporized to reduce the pressure in the head space above the free surface of volatile liquid in the reservoir, the reduced pressure in the head space reduces the liquid pressure on the side 12a of the element 12. This creates a pressure difference across the thickness of the element 12 and the element 12 can be caused to deflect inwardly of the reservoir and such deflection can stress the element 12 and cause said element to fail and tear.

Further, because of its delicate nature, the element 12 is susceptible to damage by careless handling.

Figure 4:
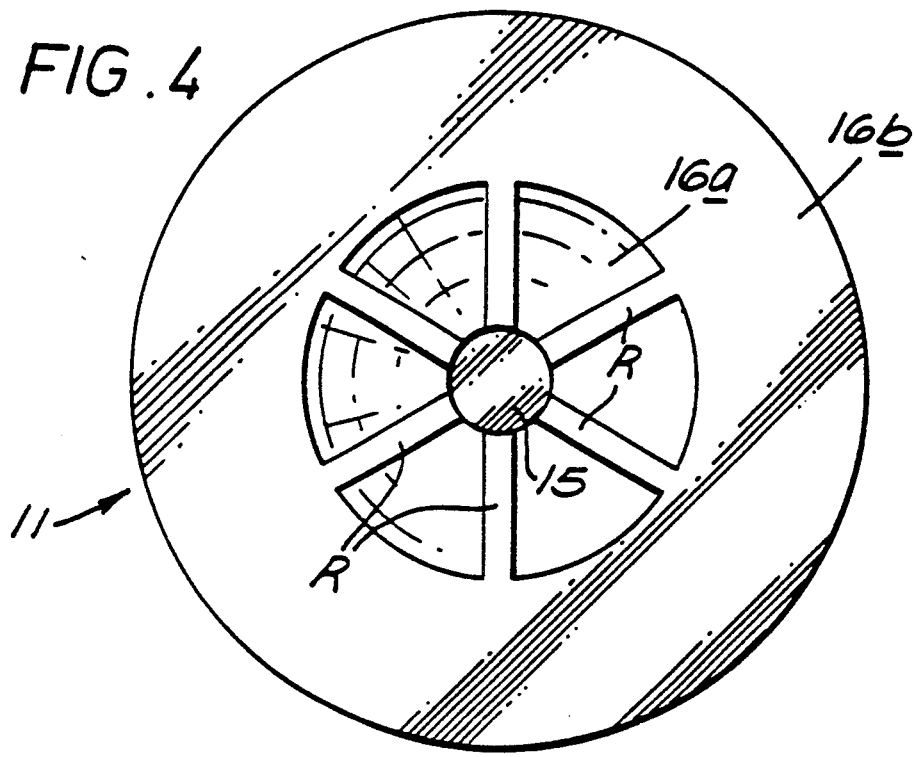
FIG. 4 shows a preferred modification for the reservoir housing shown in FIGS. 1, 2 and 3, viewed in the direction of the Arrow A.

FIG. 4 shows one form of modification for the device illustrated in FIGS. 1 and 2 for giving additional support to the element 12.

In the modified form for the housing 11 shown in FIG. 4 six radial ribs R, integral with the inner annulus flange part 16a, extend in the direction of the axis of the housing 11 to the plane of that surface of the annular flange part 16b to which the element 12 is bonded. Thus, the free surface of the ribs R in the plane of the flange part 16b can be engaged by the element 12 and supported thereby.

It should be noted that all six of the ribs R are independent. The ribs do not intrude into the diameter d1, and therefore said ribs offer no restriction to the flow of volatile liquid to any part of the element 12.

Another method for supporting the element 12 is disclosed in FIGS. 5, 6 and 7.

The device shown in FIGS. 5, 6 and 7 of the drawings generally comprises a reservoir housing 41, a support member 42, a vapour-permeable, liquid-impermeable element 43 and a liquid-impermeable vapour-impermeable barrier element 44.

The reservoir housing 41 comprises a body of revolution defined by a cylindrical wall 45, closed at one end by an end wall 46, with a flange 47 extending generally radially from that end of cylindrical wall 45 remote from the end wall 46.

The flange 47 comprises an inner annular part 47a and an outer annular part 47b, the outer annular part 47b lying in a plane at right angles to the axis of the housing 41 and the annular part 47a being inclined to the plane of the annular part 47b.

The housing 41 further includes a cylindrical wall 48 which extends from the peripheral edge of the annular flange part 47b, in opposite direction to the cylindrical wall 45.

As with the embodiment shown in FIGS. 1, 2 and 3 the housing 41 may be made from any material inert with respect to the volatile liquid to be dispensed but preferably said housing 41 comprises a plastics material, most preferably a see-through plastics material and through which the level of the volatile liquid within the casing 41 can be seen.

The support member 42 is generally annular in configuration with an upstanding central region 42a, the external diameter of which is slightly less than the internal diameter of the cylindrical wall 48 of the housing 41 so that said central region 42a can enter into the housing 11 within the cylindrical wall 48. Outwardly of said central region 42a the support member 42 is of reduced thickness and defines an annular flange 42b having a diameter greater than the maximum diameter of the housing 41.

The central region 42a of the support member 42, within a diameter substantially equal to the diameter of the junction of the annular flange part 47a with the annular flange part 47b, is pierced by a number of apertures 42c in the form of segments, which define slender ribs 42d extending radially inwardly to a boss 42e centrally of the support member 42.

The vapour-permeable, liquid-impermeable element 43 in the FIG. 5 embodiment comprises a laminate including a liquid-permeable layer 43a and a vapour-permeable, liquid-impermeable layer 43b.

The barrier layer 44 is of dish-like form and may be made from an identical material to the barrier 13 in the FIG. 1 embodiment. The barrier element 44 may include a small finger tag 44a at one peripheral region to assist in peeling the said barrier layer 44 from the device when the device is to be brought into use.

To assemble the device illustrated in FIG. 5 the vapour-permeable, liquid-impermeable element 43 is bonded to the support member 42, to define the desired area of the element 43 within the annular bonding to be exposed to wetting by the volatile material in the reservoir.

The element 43 may be bonded to the support member 42 only by the annular bond, in similar manner to the FIG. 1 embodiment, but preferably the whole of the area of the support member 42 within the annular bond is bonded to the element 43.

This may be achieved using the well known technique of in-mould labelling. Thus the pre-formed laminate 43 is placed in the base mould for the support member 42 and hot molten plastics material is injected into the mould. Upon cooling, the integrally-bonded composite element 42, 43 is removed from the mould.

Only certain grades of plastics are suitable for this process, and the injection temperature and pressure have to be carefully controlled; certain polymeric copolymers were found to be suitable, for example a copolymer of polypropylene with polyethylene, although a homopolymer might also be used. Similarly, the material of liquid-permeable layer 43a of the laminate 43 presented to the hot molten plastics material has to be selected so that it is sufficiently porous to key to the plastics material, which must semi-permeate it.

When the in-mould labelling technique has previously been used in labelling technology, one surface of the label would normally have been completely coated with plastics material and unsupported areas of label would not have been left, as in the case here when forming the apertures 42c in the support member 42, which leave unsupported area of the laminate 43.

The bonded elements 42 and 43 are then assembled with the reservoir housing 41, the central region of the support member 42 being entered into the annular recess in the reservoir housing 41 defined by the annular wall 48, and said support member 42 is secured with the housing 41 by, for example, an adhesive.

The barrier element 44 is then sealed to the annular region 42a of the support member 42 radially outwardly of the element 43, and the assembly is complete.

The reservoir housing 41 may be charged with volatile liquid by either of the methods disclosed hereinbefore with respect to FIG. 1.

To bring the device into use it is only necessary to remove the peelable barrier layer 44, when volatile liquid in the reservoir housing 41 and wetting the element 43 within the bonding of the element 43 with the support member 42 will vapourize and the vapours of the volatile liquid will issue from the vapour-permeable layer 43a of the element 43.

At all times the element 43 is supported by the support member 42 and is thus protected against accidental damage.

The device shown in FIG. 5 may conveniently be used in the holder 22 to 30 illustrated in FIG. 8.

It will now be appreciated that the device according to the present invention, in providing a housing presenting a flange to which the vapour-permeable element can be bonded in a multiplicity of different positions each of which presents a surface area of the element within the bond individual thereto, allows a single housing to be capable of dispensing any one of a wide range of volatile materials, having different desired rates of vapour release, it being only necessary to determine the surface area of the element to be wetted by the volatile liquid to give the desired rate of vaporization and to bond the element to the flange of the housing in a position to expose the said desired surface area to the selected volatile material to be dispensed.

We claim:

1. A device for dispensing a volatile liquid as a vapour, comprising a reservoir housing defining a reservoir open at one end and a vapour-permeable element bonded to said housing to close the open end of said reservoir, in which said reservoir housing defines an outwardly extending flange surrounding the open end of said reservoir and the vapour-permeable element is bonded to said flange to expose an area of the vapour-permeable element bounded by the bond, wettable by the volatile liquid in the reservoir and capable of affording a desired rate of evaporation for the volatile liquid to be dispensed, and in which the area of the flange engageable by the said vapor-permeable element is greater than twice the greatest cross-sectional area of the reservoir in planes parallel with the flange.

2. A device according to claim 1, in which said flange is an annular flange, the vapour-permeable element has a circular periphery and is bonded to the flange along an annulus of said element, the inner diameter of said annulus being variable to vary the area of the vapour-permeable element within said inner diameter wettable by the volatile liquid.

3. A device according to claim 1 or 2 in which the area of the flange engageable by said vapour-permeable element is greater than four times the greatest cross-sectional area of the reservoir in planes parallel with the flange.

4. A device according to claim 1, in which said vapour-permeable element is a liquid-impermeable element.

5. A device according to claim 4, in which said vapour-permeable element is of laminate construction comprising a liquid-permeable layer and a vapor-permeable, liquid-impermeable layer.

6. A device according to claim 5, in which said vapour-permeable element is bonded to the flange by an adhesive material.

7. A device according to claim 5, in which said reservoir housing has an opening which is closeable by a vapour-permeable element and has an area greater than the mean cross-sectional area of the reservoir in planes parallel to the plane of the vapor-permeable element.

8. A device according to claim 7, in which said reservoir housing defines two reservoir parts in open communication, a first reservoir part being adjacent the vapour-permeable element and a second reservoir part being remote from said vapor-permeable element, said first reservoir part having a mean cross-sectional area greater than the mean cross-sectional area of the second reservoir part in planes parallel to said varpour-permeable element.

9. A device according to claim 8, in which central axes of said first and second reservoir parts lie on a common axis.

10. A device according to claim 9, in which said first reservoir part reduces in cross-sectional area, in planes parallel to said vapour-permeable element, from the plane of said element towards the second reservoir part.

11. A device according to claim 10, in which said second reservoir part is of substantially uniform cross-section.

12. A device according to claim 11, in which the mean cross-sectional area of the second reservoir part is less than 80% of the mean cross-sectional area of the first reservoir part.

13. A device according to claim 12, in which the mean cross-sectional area of the second reservoir part is less than 60% of the means cross-sectional area of the first reservoir part.

14. A device according to claim 8 or 11, in which said flange includes two annular regions, an outer annular region lying in a plane at right angles to the reservoir axis and to which the vapour-permeable element is bonded, and an inner annular region defining the first reservoir part.

15. A device according to claim 14, in which the inner annular regions of said flange space the plane of the outer annular region of said flange from the second reservoir.

16. A device according to claim 4 or 5, which additionally comprises support means arranged to support that area of the vapour-permeable element exposed to the reservoir.

17. A device according to claim 16, in which said support means comprise ribs presented by said flange.

18. A device according to claim 16, in which said support means comprise a support member between said reservoir housing and said vapour-permeable element.

19. A device according to claim 18, in which said support member is bonded to said vapour-permeable element and to said reservoir housing.

20. A device according to claim 18, in which the support member is moulded integral with said vapour-permeable element.

21. A device according to claim 18, in which said support member defines a plurality of apertures through its thickness and areas of said element exposed through said apertures are exposed to wetting by the volatile liquid in said reservoir.

22. A combination comprising a device according to claim 1 or 4 and a holder for said device, in which the holder is arranged to totally enclose the device and to support the device with its vapour-permeable element lower most and exposed to a volume within said holder, said holder including apertures which vent said volume to the surrounding atmosphere.

23. The combination according to claim 22, in which said holder comprises a base part, within which the device is supported, and a removable lid which, when lifted, allows said device to be placed in, and removed from, the holder.

* * * * *